(12) United States Patent
Martin et al.

(10) Patent No.: US 7,337,778 B2
(45) Date of Patent: *Mar. 4, 2008

(54) APPARATUS WITH AUTOMATIC RESPIRATION MONITORING AND DISPLAY

(75) Inventors: Dion Charles Chewe Martin, Concord (AU); Jeffrey Peter Smith, Torrance, CA (US)

(73) Assignee: Resmed Limited, Bella Vista, NSW (AU)

( * ) Notice: Subject to any disclaimer, the term of this patent is extended or adjusted under 35 U.S.C. 154(b) by 133 days.

This patent is subject to a terminal disclaimer.

(21) Appl. No.: 11/110,244

(22) Filed: Apr. 20, 2005

(65) Prior Publication Data

US 2005/0178384 A1 Aug. 18, 2005

Related U.S. Application Data

(63) Continuation of application No. 09/596,730, filed on Jun. 16, 2000, now Pat. No. 6,895,963.

(60) Provisional application No. 60/139,516, filed on Jun. 16, 1999.

(51) Int. Cl.
*A61M 16/00* (2006.01)
*A62B 7/00* (2006.01)
*F16K 31/02* (2006.01)

(52) U.S. Cl. .............................. 128/204.21; 128/204.18

(58) Field of Classification Search ........... 128/204.18, 128/204.21–204.23, 204.26, 204.29; 345/440–440.2
See application file for complete search history.

(56) References Cited

U.S. PATENT DOCUMENTS

| 4,540,000 | A | * | 9/1985 | Doherty et al. ............. 600/509 |
| 4,630,614 | A | | 12/1986 | Atlas |
| 4,713,558 | A | | 12/1987 | Russell |
| 4,957,107 | A | | 9/1990 | Sipin |
| 5,134,995 | A | | 8/1992 | Gruenke et al. |
| 5,148,802 | A | | 9/1992 | Sanders et al. |
| 5,199,424 | A | | 4/1993 | Sullivan et al. |
| 5,245,995 | A | | 9/1993 | Sullivan et al. |
| 5,259,373 | A | | 11/1993 | Gruenke et al. |

(Continued)

FOREIGN PATENT DOCUMENTS

WO    WO 84/02641    7/1984

(Continued)

*Primary Examiner*—Danton D. DeMille
*Assistant Examiner*—Kristen C. Matter
(74) *Attorney, Agent, or Firm*—Gottlieb Rackman & Reisman PC

(57) ABSTRACT

A respiratory device is provided with a display showing a respiration signal related to a breathing pattern of a patient. This signal is derived from the difference between a sensed signal indicative of the respiration and airflow generated by the device and a baseline signal. The parameter is adjusted so that the respiration signal is restricted to a predetermined dynamic range. A short term average of the respiration signal (taken over about 0.5 seconds) and a long term average of respiration signals (taken over about 12 seconds) are calculated based on the CPAP measure. These averages are used to monitor the dynamic change in the respiration signal. If a large variation in either average is detected, the baseline is set to a value selected to rapidly reduce the respiration signal to a lower offset.

9 Claims, 6 Drawing Sheets

U.S. PATENT DOCUMENTS

| | | |
|---|---|---|
| 5,483,969 A | 1/1996 | Testerman et al. |
| 5,669,379 A * | 9/1997 | Somerson et al. ..... 128/204.21 |
| 5,735,285 A * | 4/1998 | Albert et al. ............... 600/509 |
| 5,740,795 A | 4/1998 | Brydon |
| 5,956,013 A * | 9/1999 | Raj et al. .................... 345/208 |
| 6,158,432 A | 12/2000 | Biondi et al. |

FOREIGN PATENT DOCUMENTS

| | | |
|---|---|---|
| WO | WO 98/12965 | 4/1998 |
| WO | WO 99/61088 | 12/1999 |

* cited by examiner

Treatment pressure-ramp with Auto-Baseline disabled – as the treatment pressure increases, the signal eventually exceeds the available dynamic range.

Treatment pressure-ramp with superimposed breath activity, Auto-Baseline disabled – as the treatment pressure increases, the signal eventually exceeds the available dynamic range.

Treatment pressure change with breath activity, Auto-Baseline enabled – the signal's baseline is automatically adjusted to keep the signal within the available dynamic range Gradual pressure change with Auto-Baseline enabled – minor automatic baseline corrections bring signal close to centre of dynamic range

APPARATUS WITH AUTOMATIC RESPIRATION MONITORING AND DISPLAY

This application is a continuation of U.S. application Ser. No. 09/596,730 filed Jun. 16, 2000, now U.S. Pat. No. 6,895,963, now allowed, which claims priority to U.S. provisional application Ser. No. 60/139,516 filed Jun. 16, 1999.

BACKGROUND OF THE INVENTION

A. Field of Invention

The invention relates to respiratory systems such as Non-Invasive Positive Pressure Ventilation (NIPPV), nasal Continuous Positive Airway Pressure (CPAP) and other similar apparatus, used, for example, in the treatment of Sleep Disordered Breathing (SDB) or Obstructive Sleep Apnea (OSA). More particularly, this invention pertains to a respiratory apparatus which uses an automatic baseline tracking technique to monitor and display a patient's respiration, for example during a CPAP titration session of a sleep investigation.

B. Description of the Prior Art

CPAP, NIPPV and similar types of respiratory apparatus function to supply clean breathable gas (usually air, with or without supplemental oxygen) at a prescribed pressure or pressures, synchronously with a patient's respiration. A suitable CPAP apparatus in which the present invention may be incorporated is, for example, the Sullivan® V made by ResMed Ltd. of North Ryde NSW, Australia.

A respiratory apparatus typically includes a blower, an air filter, a mask or other similar patient interface, an air delivery conduit connecting the blower to the mask, and a microprocessor-based control unit. The blower generally includes a servo-controlled motor and an impeller and is used to provide a flow of pressurized air to the patient. The blower may also include a valve for discharging air. Optionally, the apparatus may include a humidifier which can apply moisture to the air supplied through the air delivery conduit. The control unit is used to control the functions of the blower, and to monitor clinical functions and other parameters associated with respiration. These parameters may be used for the diagnosis of sleep and respiratory disorders. Respiratory disorders such as apnea, snoring, and partial airflow limitations can be inferred by a clinician from the patient's respiration, the associated breathing pattern and signals from other sensors.

A convenient, established way of monitoring respiration during the diagnosis of a sleep disorder consists of analyzing pressure fluctuations obtained from nasal oxygen cannulae inserted into the patient's nares. This provides an indication of respiration flow. If upper-airway irregularities of a significant number are recorded, a CPAP titration session may be ordered. The goal of a CPAP titration session is to determine what level of CPAP treatment is needed to abolish the bulk of the patient's upper-airway irregularities. Throughout the session the CPAP level (pressure) is manually adjusted to resolve the irregularities. During such a session, respiration may be assessed by interpreting the mask pressure signal, a complex pressure signal consisting of the following components: (a) a CPAP component related to the positive airway pressure induced by the blower and having a very low frequency (in the order of 0-0.1 Hz) and high amplitude (in the order of 2-30 cm $H_2O$); (b) a respiration component related to the normal respiration of the patient and having a relatively low frequency (of about 0.01 Hz) and low amplitude, generally not exceeding 10 mm of $H_2O$; and possibly (c) a component associated with snoring and having a high frequency in the range of 30-200 Hz and a low amplitude in the order of mm of $H_2O$. For diagnostic purposes, it is desirable to generate an output signal indicative of the last two components (b) and (c) to derive the respiration sequence referred to herein as the respiration signal.

Prior art respiration monitoring systems use high-pass filtering to separate the desired components from the complex pressure signal. This technique can be unsatisfactory because: (1) if the high-pass filter excludes low-frequency components of the respiratory signal, it will compromise the integrity of the monitored signal; (2) it is slow to track changes in CPAP component, particularly fluctuations due to leaks which are often known to cause step changes in the pressure signal; and (3) if performed in software, it requires high resolution and extensive signal processing.

Another known technique for deriving and monitoring a respiration signal uses a DC-coupled response amplifier without high-pass filtering of the complex pressure signal. The disadvantage of a DC-coupled technique is that the CPAP component appears as a DC offset which must be subtracted from the complex pressure signal so that the respiration signal does not exceed the dynamic range of the measurement system. During a titration study, each adjustment of the CPAP treatment pressure may demand an adjustment of the DC offset, if the respiration signal is to stay within the dynamic range of the monitoring system. Typically a special manual knob is provided for this purpose which allows an operator to eliminate the DC offset. Hence, using a DC-coupled response amplifier is time-consuming and requires a manual operation of the respiratory apparatus, additional training, and constant attention by an operator.

If the CPAP component generated by the blower is continuously known by the respiration monitoring system, an alternate technique would be to subtract this CPAP component from the complex pressure signal sensed in the mask, theoretically leaving just the respiration signal. This technique is impractical because leaks may occur, causing the pressure in the mask to deviate significantly from the pressure set for the blower and because the blower may not be in constant communication with the sensing device and, therefore, the CPAP component may not always be present.

OBJECTIVES AND SUMMARY OF THE INVENTION

In consideration of the above, it is an objective of the present invention to provide a respiratory apparatus in which a respiration signal is generated, the signal being automatically adjusted to lie in a predetermined range.

A further objective is to provide a respiratory apparatus capable of displaying a respiration signal to a clinician by calculating a baseline correction and automatically adjusting the baseline to track long and/or short term variations of the respiration signal.

A further objective is to provide a respiratory apparatus which generates a respiration signal indicative of a patient's respiration without the need for an operator to compensate manually for pressure variations produced by the apparatus.

A key advantage of the invention to a clinician performing a sleep study is that the need for intervention during the operation of the subject respiratory apparatus is reduced or eliminated. The present invention simplifies respiration monitoring without sacrificing signal integrity.

A further advantage of the subject invention is that it provides a respiratory apparatus which displays a respiration signal as an indication of the upper airway resistance in a patient, the apparatus being reliable and easy to use.

Other objectives and advantages of the invention shall become apparent from the following description.

Briefly, a respiratory apparatus constructed in accordance with this invention includes a blower providing a flow of pressurized air to the patient, a patient interface (such as a mask receiving air from the blower), a control unit for managing the blower, and a display to show a respiration signal generated by the control unit. The control unit includes a pressure transducer for sensing the actual instantaneous pressure within the patient interface and for converting this pressure to an electrical pressure signal, and a summer which subtracts a baseline pressure signal from the pressure signal to generate a respiration signal. The baseline signal can be adjusted automatically or manually. For the automatic adjustment of the baseline signal, long term and short term averages of the respiration signal are calculated. These averages are used to adjust the baseline signal in a manner that insures that the respiration signal remains within the predetermined range. Adjusting the baseline pressure signal compensates for changes in the respiration signal caused by the operation of the blower (i.e., the CPAP component) or other factors, such as the development of a sudden leak.

DETAILED DESCRIPTION OF THE INVENTION

Figure 1:
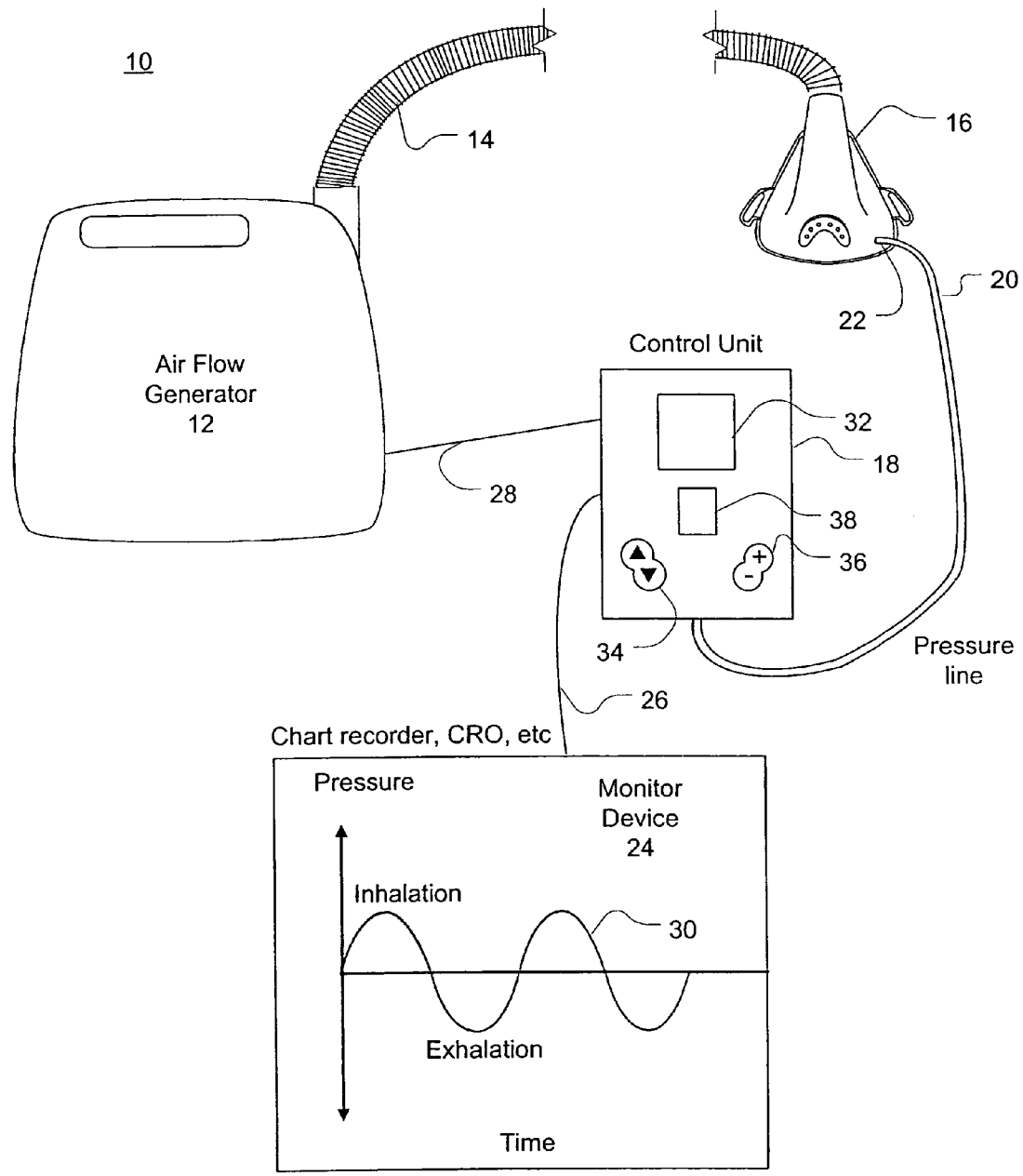
FIG. 1 shows the elements of a respiratory apparatus constructed in accordance with this invention.

Referring now to FIG. 1, a respiratory apparatus 10 constructed in accordance with this invention includes a blower 12 adapted to provide pressurized air, a flexible conduit 14, a mask 16 and a control unit 18. The control unit 18 is connected to the mask 16 by a flexible pressure line 20 via a pressure port 22. The control unit 18 is also connected to a display 24 and to the blower 12 by respective cables 26 and 28. The blower 12 may be a CPAP flow generator such as the one marketed under the name Sullivan® V generator made by ResMed Ltd. of North Ryde, NSW, Australia.

The mask 16 is used to represent generically any suitable patient interface such as a nasal mask or a full face mask, such as the Mirage® mask made by ResMed, or other similar devices designed to deliver air from the generator 12.

The display 24 is designed to indicate graphically the operation of the apparatus 10 and the respiration of the patient, as indicated, for example, on chart 30. The display 24 may be a chart recorder, a CRT, a PC or a similar device.

Preferably, control unit 18 is programmable and includes a screen 32 and two rocker switches 34 and 36. The first rocker switch 34 is marked with up and down arrows, as shown, and is used to select a mode of operation from a menu on screen 32. The other switch 36 is marked with + and − symbols and may be used to select and change the values of certain programmable parameters associated with the operation of the apparatus 10. Finally, an override switch 38 is also provided on control unit 18 to override the operation of the apparatus. Control unit 18 monitors the operation of the blower 12 and generates a signal indicative of the respiration of the patient for display.

The apparatus 10 may be used to perform sleep studies and may be installed in a hospital, clinic, or patient's home. For this purpose, the control unit 18 monitors the respiration of the patient through mask 16 and configures the blower 12 to provide a controlled pressurized air into the mask 16 through conduit 14 when required, as is well known in the art.

Figure 2:
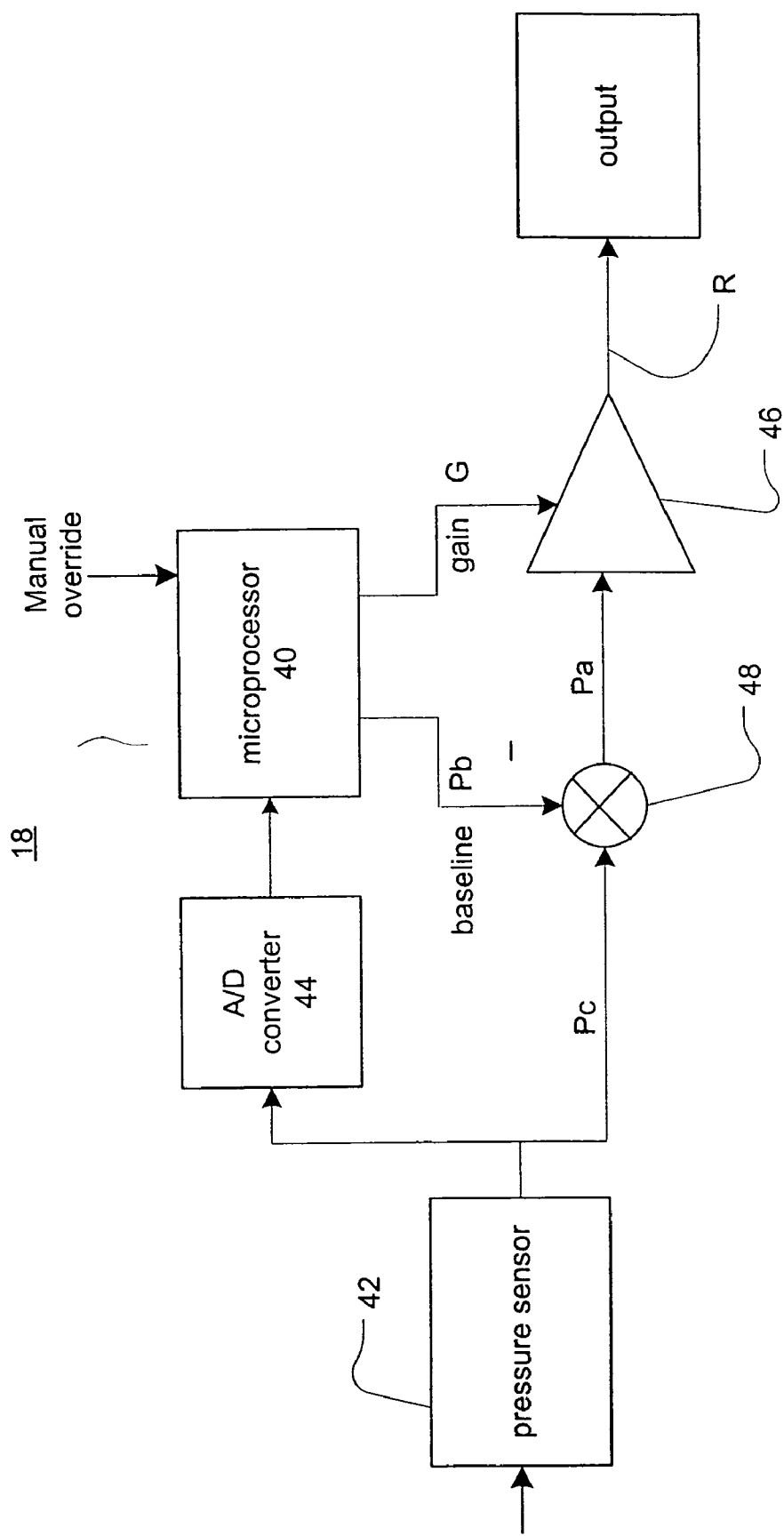
FIG. 2 shows a block diagram for a control unit for the respiratory apparatus of FIG. 1.

As shown in FIG. 2, the control unit 18 includes a microprocessor 40, a pressure sensor 42, an analog-to-digital (A/D) converter 44, an amplifier 46 and a summer 48. The pressure sensor 42 is used to detect the current pressure within the mask 16 and to send a corresponding current pressure signal Pc to the A/D converter 44 and to the summer 48. The microprocessor 40 uses the current pressure Pc in the mask to derive a baseline pressure signal Pb which is summed with signal Pc.

More particularly, the summer 48 subtracts the baseline pressure signal Pb from the current pressure Pc. The resulting adjusted pressure Pa (Pa=Pc−Pb) is fed to the amplifier 46 which amplifies it at a gain G (selected by the microprocessor) to generate a respiration signal R.

Figure 3:
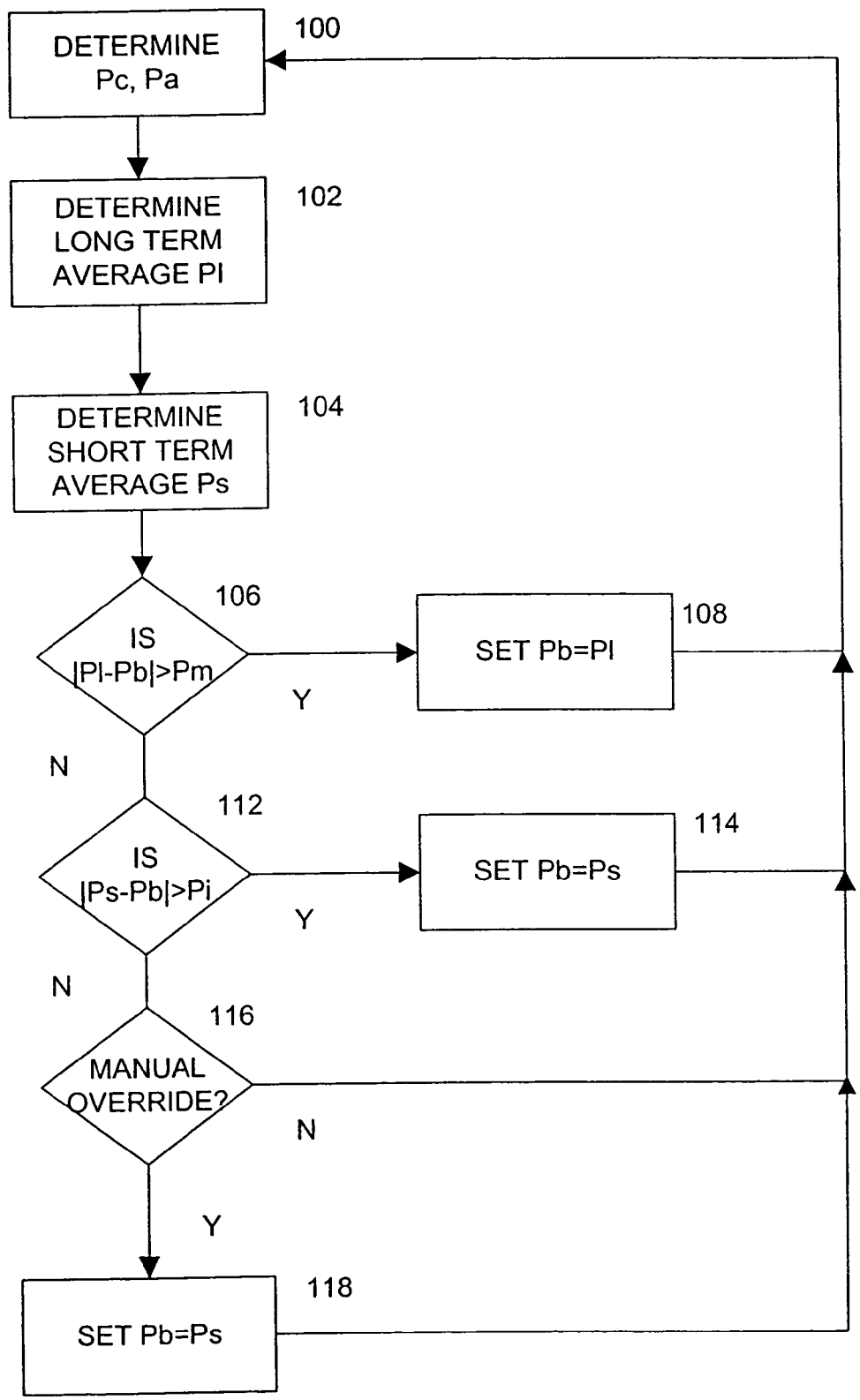
FIG. 3 shows a flow chart illustrating the operation of the respiratory apparatus of FIGS. 1 and 2.

Referring to FIG. 3, during operation of the apparatus the baseline pressure signal Pb is determined as follows. In step 100, a current pressure Pc is first determined dynamically by sensor 42. Using this signal Pc, and a nominal or default value Pb0 (selected as discussed below), the signal Pa is calculated using formula Pa=Pc−Pb. This signal Pa is then amplified at gain G to obtain respiration signal R. In step 102 a long term average parameter P1, which is indicative of a long term average of the respiration signal R, is calculated. Parameter P1 may be a moving average of the respiration signal taken over the previous 12 seconds.

In step 104, microprocessor 40 determines a short term average parameter Ps indicative of a short-term average of the respiration signal R. Parameter Ps may be a moving average of the respiration signal taken over the previous 0.5 seconds. Parameter Ps is effectively indicative of the transient pressure noise within the mask.

These calculations are made by the control unit 18 to determine pressure variations within system 10 attributable to extraneous causes, i.e., variations caused by factors other than the respiration of the patient. For example, if the blower 12 is a CPAP flow generator, then the pressure variations may be due to the generated CPAP (continuous positive airway pressure) air flow. The baseline pressure signal Pb is therefore set using these pressure variations, as discussed below.

Next, the microprocessor 40 performs three checks and adjusts the baseline signal Pb (if necessary) to compensate for extraneous air pressure variations. The first check (step 106) determines the deviation between the current baseline signal Pb and the CPAP. This check comprises taking the absolute difference between the long term parameter P1 and the current baseline pressure signal Pb, and comparing this absolute difference to a predetermined threshold pressure Pm. This threshold pressure Pm maybe a fraction (for example, ⅛th) of the output dynamic range of amplifier 46. If this absolute difference is larger than Pm, then in step 108 the baseline pressure Pb is set to the parameter P1.

If no significant deviation between the current signal Pb and CPAP is found in step 106, (i.e., 1P1−Pb1<Pm) then a second check is performed in step 112. Under certain conditions, the CPAP can change rapidly. This rapid change may be due, for example, to an abrupt leak in the mask 16, or because the blower 12 is activated and starts pumping air into the mask. The purpose of this second check is to insure that the baseline signal Pb tracks the CPAP during its short-term excursion. More specifically, in step 112 a test is performed to determine whether the absolute difference between the short term average pressure parameter Ps and the baseline pressure signal Pb has exceeded a threshold pressure Pi for a period of Ti. The period Ti is defined as the maximum time period for which a healthy adult can sustain a continuous inspiration or expiration. Typically Ti is about 6 seconds and Pi is about 3 cm $H_2O$. Alternatively, the threshold pressure Pi may also be set as a fraction of the dynamic range of the amplifier.

If in step 112 the absolute difference |Pb−Ps| is determined to be greater than Pi for the last Ti seconds, then in step 114 the baseline pressure Pb is set to the parameter Ps. The process then recycles to step 100 with the new value for Pb being used instead of Pb0.

The third check is performed in step 116. This step is provided as a means for a clinician to override the current value of the baseline signal Pb. For example, when the clinician activates pushbutton 38 (FIG. 1), the microprocessor 40 receives an override control signal. If this override signal is sensed, then the baseline pressure signal Pb is set to Ps (step 118). The check for an override signal is shown step 116 as following a 'NO' decision in step 112, however, it may be performed at any other time.

When in automatic mode, the control unit operates in accordance with the flow chart of FIG. 3, as described above. However, certain parameters, such as the initial value of the baseline signal Pb and the gain G may be adjusted by the clinician. For example, baseline signal Pb may be set to a nominal or default level Pb0 in the range of 0-35 cm $H_2O$ using switch 36. If no manual override is detected in step 116 then the process recycles to step 100.

The effects of adjusting the baseline pressure signal Pb in the manner described in FIG. 3 are best understood by reference to the waveforms of FIGS. 4A-E. In each of these figures, the current pressure (Pc) within the mask 16 is measured by pressure sensor 42 and processed by the circuit shown in FIG. 2. The respiration signal R of amplifier 46 is depicted as a function of time. Conventionally, a higher mask pressure (corresponding to exhalation) is shown as a negative signal (corresponding to a mask pressure) while inhalation is indicated in the Figures (when applicable) as a positive signal. When the respiration signal reaches the edge of the dynamic range of the amplifier it is clipped, as discussed in more detail below.

Figure 4A:
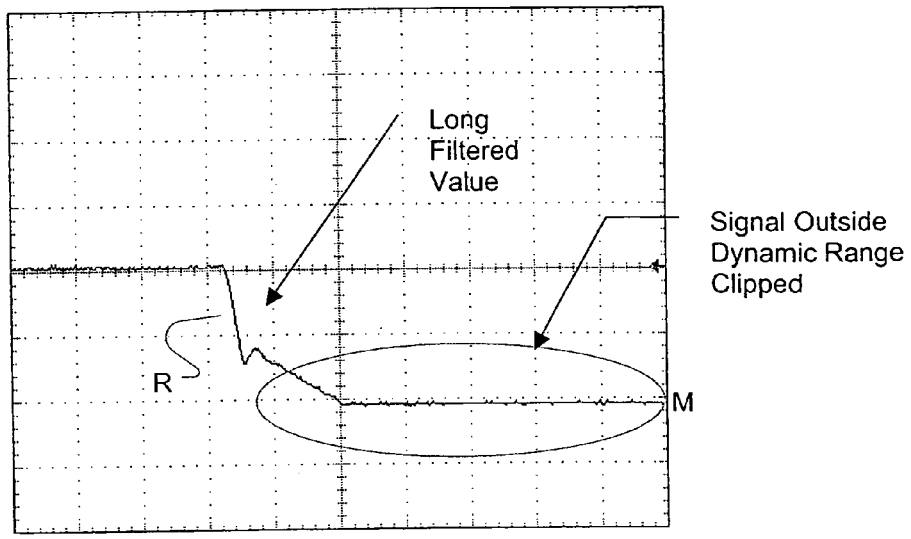
FIGS. 4A-4E show time dependent graphs of a respiration signal generated by the control unit of FIG. 2 for various operating conditions.

FIG. 4A shows the operation of the apparatus 10 when mask 16 is not secured to a patient and the baseline adjustment feature is disabled. As indicated in this figure, as signal R increases, it eventually reaches a maximum threshold M defined by the dynamic range of the amplifier 46. The respiration signal R is clipped at level M.

Figure 4B:
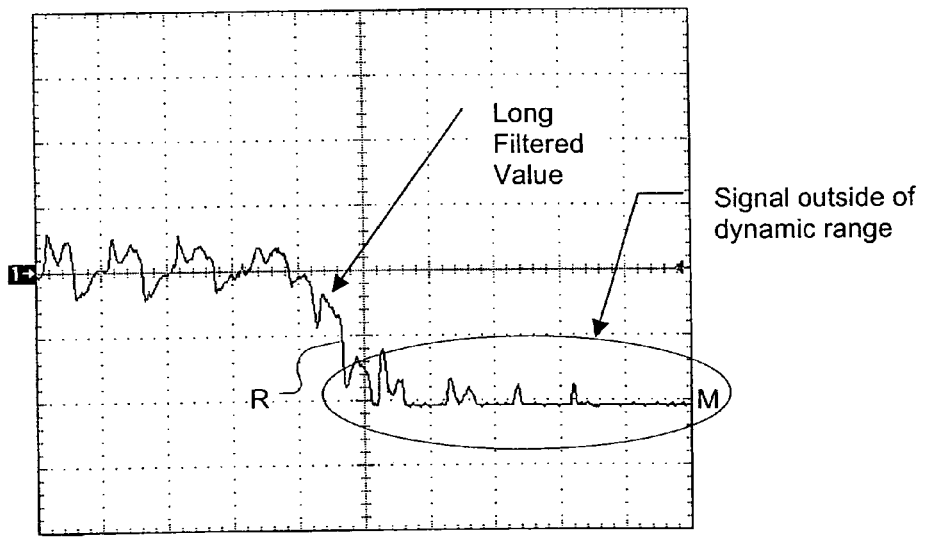

FIG. 4B is similar to FIG. 4A with the exception that the mask 16 has been secured to a patient and the respiration component is present. When signal R reaches level M, it is clipped.

Figure 4C:
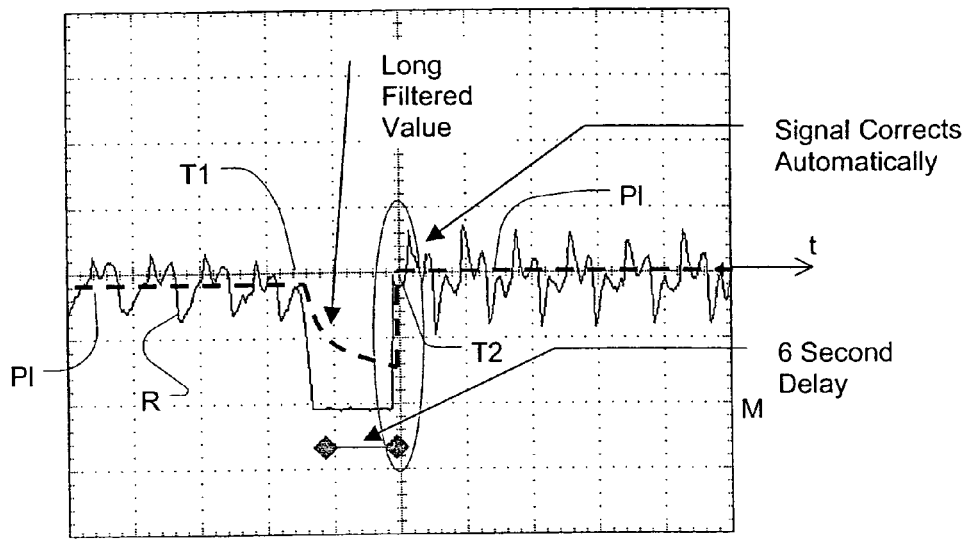

FIG. 4C shows the respiration signal R and its long term average P1 when the baseline adjustment feature has been activated. As this figure depicts, prior to t=T1, the long term average P1 is relatively stable and baseline pressure signal Pb is set to its default value Pb0. At t=T1 the pressure signal increases rapidly, toward M, and stays at that level. Therefore both P1 and Ps start increasing. As soon as P1 exceeds Pb by more than the preselected threshold Pi, the baseline pressure is set to P1 (steps 106, 108). But since P1 increases relatively slowly and since Pa is very high, initially this change in Pb has no effect. After six seconds in this mode, however, the criteria of step 112 is met, and Pb is set to Ps (steps 112, 114). As a result, at t=T2 the respiration signal R is corrected automatically so that is centered around P1.

Figure 4D:
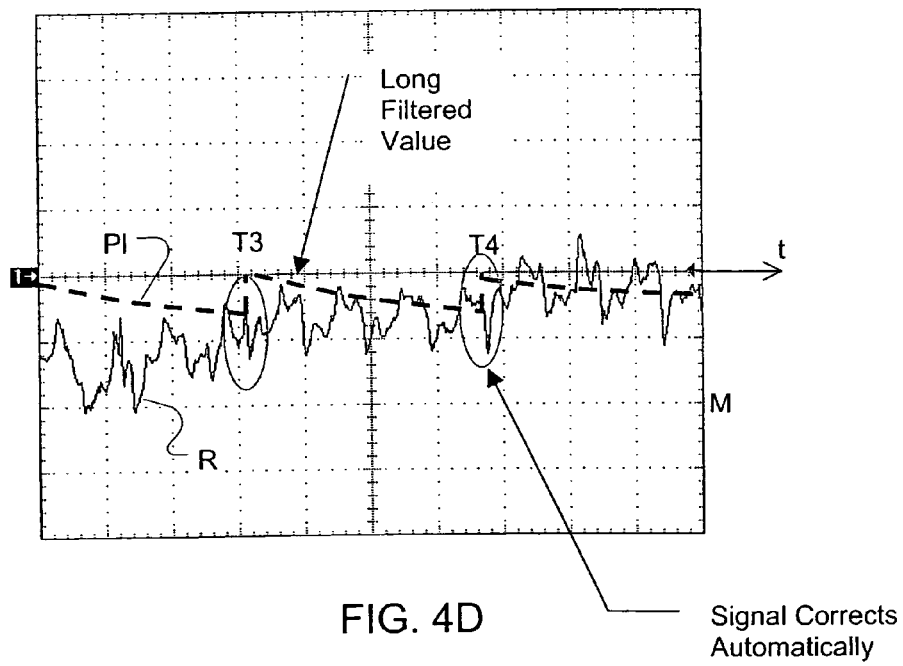

FIG. 4D shows the respiration signal R staying below the threshold level M but drifting slowly. Therefore, the long term average P1 drifts as well. When P1 becomes too large, Pb is adjusted as at T3 and T4 causing the respiration signal R to approach the horizontal axis. In this manner, the respiration signal R is maintained within the dynamic range of the amplifier 46.

Figure 4E:
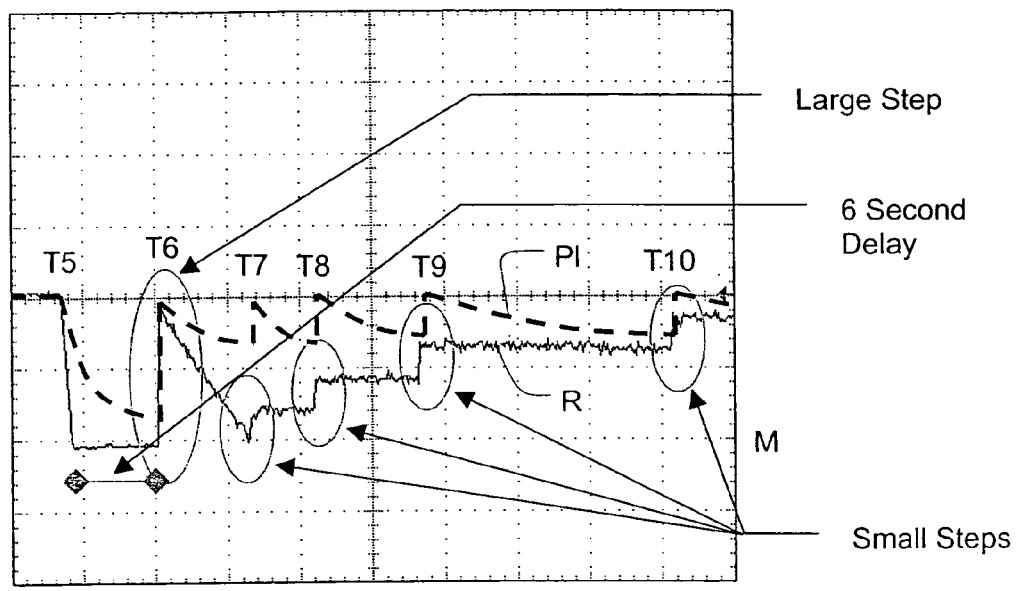

FIG. 4E shows a sequence wherein initially at t=T5 there is a rapid change in the current pressure Pc. This change is handled by the system in the same manner as described above regarding FIG. 4C. This rapid change is corrected at t=T6 and is followed by a gradual pressure change. The gradual pressure change is corrected at t=T7, T8, T9 and T10 as shown.

Curves similar to those of FIGS. 4A-4E can be shown on display 24 so that a patient's breathing and the operation of the baseline adjustment circuit of FIG. 2 can be monitored.

At any time, the clinician may activate the override pushbutton 38 which immediately sets the baseline pressure signal Pb to the short term average Ps, thereby rapidly centering the respiration signal R to the middle of the effective dynamic range of the system.

In summary, the subject device proffers the following advantages:

a) It utilizes a DC-coupled amplifier, thereby insuring signal spectrum that extends to 0 Hz.

b) Its automatic baseline adjustment feature can be turned off at will, leaving the clinician with the standard manual baseline adjustment.

c) Changes in the respiration signal are presented clearly to the clinician. In one embodiment, automatic adjustments are indicated by explicit markers corresponding to changes in the baseline pressure signal.

d) Adjustments of the baseline pressure signals are made only to prevent the respiration signal from moving outside the dynamic range of the amplifier.

e) Adjustments in the baseline pressure signal are performed fast enough to track typical automatic or manual-titration without having the respiration signal R exceed the dynamic range of its amplifier.

f) Tracking does not change as a result of respiratory activity because it follows CPAP changes only.

g) For very rapidly changing CPAP pressures (e.g., during the start-up period of the blower) where automatic tracking may fail to keep up, a manual baseline capture is provided to allow instantaneous baseline adjustments.

The invention has been described in conjunction with a particular type respiratory apparatus, however it may be incorporated into other kinds of devices as well. For example, in some respiratory devices respiration monitors are used which include effort sensors such as respiratory bands or suprasternal notch sensors. These effort sensors infer the effort expanded by the patient during respiration and generate signals that are shown on a display. Under certain circumstances, for example when the patient moves or shifts position, the sensor signals undergo a large shift which exceeds the dynamic range of the display. The present invention may be used in such devices to cause the sensor signals to return to the dynamic range of the display.

Obviously numerous modifications may be made to this invention without departing from its scope as defined in the appended claims.

We claim:

1. A respiratory apparatus for delivering a flow of air to a patient suffering from sleep disordered breathing comprising:
    a blower that generates a flow of pressurized air;
    a patient interface adapted to deliver air from said blower to the patient;
    a display receiving and displaying a respiration signal and having a predetermined display range; and
    a control unit coupled to said patient interface and adapted to sense a breathing parameter, said control unit including a display adjusting circuit that operates on said breathing parameter to generate a respiration signal indicative of the breathing pattern of the patient; said control unit further deriving short-term and long-term averages of said respiration signal, said display adjusting circuit operating to adjust a baseline of said respiration signal in accordance with at least one of said long-term and short-term averages to restrict said respiration signal to said predetermined display range; and
    wherein said display adjusting circuit adjusts the displayed respiration signal in accordance with said long-term average in response to one set of conditions, and adjusts the displayed respiration signal in accordance with said short-term average in response to another set of conditions.

2. A respiratory apparatus for delivering a flow of air to a patient suffering from sleep disordered breathing comprising:
    a blower that generates a flow of pressurized air in accordance with a control signal;
    a patient interface adapted to deliver air from said blower to the patient;
    a display having a predetermined display range for displaying a respiration signal indicative of the breathing of the patient; and
    a control unit coupled to said patient interface for generating said control signal and being adapted to sense a parameter characteristic of the breathing of said patient and to generate said respiration signal;
    said control unit further (a) determining long-term and short-term averages of said respiration signal, (b) comparing said long-term average to the baseline of said respiration signal and changing said baseline in accordance with said long-term average if the difference between said baseline and said long-term average is equal to or greater than a predetermined value; and (c) if said difference is less than said predetermined value, then comparing said short-term average to said baseline and changing said baseline in accordance with said short-term average if the difference between said baseline and said short-term average is greater than a predetermined value.

3. The respiratory apparatus of claim 2 wherein said respiration signal is calculated by subtracting said baseline from an instantaneous representation of the breathing of said patient.

4. The respiratory apparatus of claim 3 wherein said long-term average is calculated over a period of about twelve seconds.

5. The respiratory apparatus of claim 3 wherein said short-term average is calculated over a period of about 0.5 seconds.

6. A method for presenting a derived signal indicative of a patient's breathing on a display having a predetermined display range, the method comprising the steps of:
    generating a signal representative of a parameter related to the breathing of the patient;
    determining a short-term average of said generated signal and a long-term average of said generated signal;
    determining a baseline of said generated signal;
    comparing said baseline to said long-term average and if the difference between said baseline and said long-term average is equal to or greater than a predetermined value, then changing said baseline to said long-term average;
    if the difference between said baseline and said long-term average is less than said predetermined value, then comparing said baseline to said short-term average and changing said baseline to said short-term average if the difference between said baseline and said short-term average is greater than a predetermined value; and
    displaying on said display a derived signal as a function of said generated signal and said baseline.

7. The method of claim 6 wherein said derived signal is calculated by subtracting said baseline from said generated signal.

8. The method of claim 7 wherein said long-term average is calculated over a period of about twelve seconds.

9. The method of claim 7 wherein said short-term average is calculated over a period of about 0.5 seconds.

* * * * *